(12) United States Patent
Kruse

(10) Patent No.: US 11,896,799 B2
(45) Date of Patent: Feb. 13, 2024

(54) SYSTEM AND METHOD FOR DETECTING PRESENCE OF AN INFUSION CARTRIDGE IN AN INFUSION PUMP

(71) Applicant: Tandem Diabetes Care, Inc., San Diego, CA (US)

(72) Inventor: Geoffrey Kruse, San Diego, CA (US)

(73) Assignee: TANDEM DIABETES CARE, INC., San Diego, CA (US)

( * ) Notice: Subject to any disclaimer, the term of this patent is extended or adjusted under 35 U.S.C. 154(b) by 759 days.

(21) Appl. No.: 15/467,500

(22) Filed: Mar. 23, 2017

(65) Prior Publication Data

US 2017/0246379 A1 Aug. 31, 2017

Related U.S. Application Data

(63) Continuation of application No. 13/837,661, filed on Mar. 15, 2013, now abandoned.

(51) Int. Cl.
*A61M 5/14* (2006.01)
*A61M 5/152* (2006.01)
(Continued)

(52) U.S. Cl.
CPC ........ *A61M 5/152* (2013.01); *A61M 5/14244* (2013.01); *A61M 5/145* (2013.01);
(Continued)

(58) Field of Classification Search
CPC .............. A61M 5/142; A61M 2205/14; A61M 5/14566; A61M 5/50; A61M 5/145;
(Continued)

(56) References Cited

U.S. PATENT DOCUMENTS 4,194,144 A * 3/1980 Reynolds ................ H02P 23/22
388/922
5,231,616 A 7/1993 Oliver et al.
(Continued)

FOREIGN PATENT DOCUMENTS

WO WO0130422 A1 5/2001
WO WO2010026580 3/2010
(Continued)

OTHER PUBLICATIONS

Application and File History for U.S. Appl. No. 13/837,661, filed Mar. 15, 2013, inventor Kruse.
(Continued)

*Primary Examiner* — Shefali D Patel
*Assistant Examiner* — William R Frehe
(74) *Attorney, Agent, or Firm* — Merchant & Gould, P.C.

(57) ABSTRACT

Infusion devices, systems, and methods can for detecting a presence or an absence of an infusion cartridge in an infusion pump. Embodiments may include a loading sequence, recording loading pulse width modulation (PWM) commands applied to an infusion pump motor during the loading sequence, setting a value of threshold PWM commands based on the loading PWM commands applied during the loading sequence and comparing values of operational PWM commands applied during pumping operations to the value of the threshold PWM commands. If the values of the operational PWM commands drops below the value of the threshold PWM commands by a predetermined amount, a missing infusion cartridge warning may be generated.

25 Claims, 4 Drawing Sheets

(51) Int. Cl.
*A61M 5/142* (2006.01)
*A61M 5/168* (2006.01)
*A61M 5/145* (2006.01)

(52) U.S. Cl.
CPC ..... *A61M 5/14212* (2013.01); *A61M 5/16809* (2013.01); *A61M 2205/14* (2013.01); *A61M 2205/6009* (2013.01)

(58) Field of Classification Search
CPC .............. A61M 5/152; A61M 5/14244; A61M 2205/6009; A61M 5/14212; A61M 5/16809
See application file for complete search history.

(56) References Cited

U.S. PATENT DOCUMENTS

| | | | |
|---|---|---|---|
| 5,243,983 | A | 9/1993 | Tarr et al. |
| 5,482,446 | A | 1/1996 | Williamson et al. |
| 5,551,850 | A | 9/1996 | Williamson et al. |
| 5,676,651 | A | 10/1997 | Larson, Jr. et al. |
| 5,681,285 | A | 10/1997 | Ford et al. |
| 6,269,340 | B1 | 7/2001 | Ford et al. |
| 6,582,393 | B2 | 6/2003 | Sage, Jr. |
| 6,673,033 | B1 | 1/2004 | Sciulli et al. |
| 6,909,840 | B2 | 6/2005 | Harwig et al. |
| 6,981,499 | B2 | 1/2006 | Anderson et al. |
| 6,997,202 | B2 | 2/2006 | Olander |
| 7,220,365 | B2 | 5/2007 | Qu et al. |
| 7,305,975 | B2 | 12/2007 | Reddy |
| 7,442,186 | B2 | 10/2008 | Blomquist |
| 7,471,994 | B2 | 12/2008 | Ford et al. |
| 7,605,710 | B2 | 10/2009 | Crnkovich et al. |
| 7,647,237 | B2 | 1/2010 | Malave et al. |
| 7,760,601 | B2 | 7/2010 | Igi |
| 7,922,458 | B2 | 4/2011 | Rush et al. |
| 7,922,462 | B2 | 4/2011 | Preuthun et al. |
| 7,935,105 | B2 | 5/2011 | Miller et al. |
| 7,973,667 | B2 | 7/2011 | Crnkovich et al. |
| 7,993,108 | B2 | 8/2011 | Rush et al. |
| 7,993,300 | B2 | 8/2011 | Nyholm et al. |
| 8,029,245 | B2 | 10/2011 | Rush et al. |
| 8,029,250 | B2 | 10/2011 | Rush et al. |
| 8,032,226 | B2 | 10/2011 | Miller et al. |
| 8,047,811 | B2 | 11/2011 | Rush et al. |
| 8,047,812 | B2 | 11/2011 | Rush et al. |
| 8,105,265 | B2 | 1/2012 | Demers et al. |
| 8,109,906 | B2 | 2/2012 | Smisson, III et al. |
| 8,211,093 | B2 | 7/2012 | Miller et al. |
| 8,226,374 | B2 | 7/2012 | Peterson et al. |
| 8,277,416 | B2 | 10/2012 | Gibbs et al. |
| 8,287,488 | B2 | 10/2012 | Miller et al. |
| 8,287,495 | B2 | 10/2012 | Michaud et al. |
| 8,287,514 | B2 | 10/2012 | Miller et al. |
| 8,444,592 | B2 | 5/2013 | Williams et al. |
| 8,573,027 | B2 | 11/2013 | Rosinko et al. |
| 8,876,769 | B2 | 10/2014 | Fehr et al. |
| 8,986,253 | B2 | 3/2015 | DiPerna |
| 9,603,995 | B2 | 3/2017 | Rosinko et al. |
| 2002/0018720 | A1 | 2/2002 | Carlisle et al. |
| 2005/0148938 | A1 | 7/2005 | Blomquist |
| 2007/0112301 | A1 | 5/2007 | Preuthun et al. |
| 2008/0249470 | A1 | 10/2008 | Malave et al. |
| 2009/0069746 | A1 | 3/2009 | Miller et al. |
| 2009/0069749 | A1 | 3/2009 | Miller et al. |
| 2009/0069785 | A1 | 3/2009 | Miller et al. |
| 2009/0101549 | A1 | 4/2009 | Kamen et al. |
| 2009/0107335 | A1 | 4/2009 | Wilt et al. |
| 2010/0022937 | A1 | 1/2010 | Bedingfield et al. |
| 2010/0164727 | A1* | 7/2010 | Bazargan ......... A61M 5/14244 340/573.1 |
| 2010/0192686 | A1 | 8/2010 | Kamen et al. |
| 2010/0211003 | A1* | 8/2010 | Sundar ............... A61M 5/172 604/67 |
| 2011/0071465 | A1 | 3/2011 | Wang et al. |
| 2011/0092894 | A1 | 4/2011 | Mcgill et al. |
| 2011/0125085 | A1 | 5/2011 | Mcgill et al. |
| 2011/0163125 | A1 | 7/2011 | Beavis et al. |
| 2011/0286008 | A1* | 11/2011 | Schlaeppi ......... A61M 5/1456 356/614 |
| 2012/0029468 | A1 | 2/2012 | DiPerna |
| 2012/0029708 | A1 | 2/2012 | Miller et al. |
| 2012/0029941 | A1 | 2/2012 | Malave et al. |
| 2012/0078217 | A1 | 3/2012 | Smith et al. |
| 2012/0259282 | A1* | 10/2012 | Alderete, Jr. ..... A61M 5/14244 604/131 |
| 2013/0012917 | A1 | 1/2013 | Miller et al. |
| 2013/0053816 | A1 | 2/2013 | DiPerna et al. |
| 2014/0039455 | A1 | 2/2014 | Miller |
| 2014/0137641 | A1 | 5/2014 | Brown |
| 2014/0276553 | A1 | 9/2014 | Rosinko et al. |
| 2014/0276569 | A1 | 9/2014 | Kruse |
| 2017/0246380 | A1 | 8/2017 | Rosinko et al. |

FOREIGN PATENT DOCUMENTS

| | | |
|---|---|---|
| WO | WO2011068648 | 6/2011 |
| WO | WO2012040528 | 3/2012 |

OTHER PUBLICATIONS

Search Report dated Nov. 21, 2016 for European Application No. 14768610.9.
PCT Search Report and Written Opinion dated Jul. 1, 2014 for PCT Application No. PCT/US2014/018735 filed Feb. 26, 2014.

* cited by examiner

SYSTEM AND METHOD FOR DETECTING PRESENCE OF AN INFUSION CARTRIDGE IN AN INFUSION PUMP

RELATED APPLICATION

This application is a continuation of application Ser. No. 13/837,661 filed Mar. 15, 2013, which is hereby fully incorporated herein by reference.

BACKGROUND

There are many applications in academic, industrial, and medical fields, as well as others, that benefit from devices and methods that are capable of accurately and controllably delivering fluids, including liquids and gases that have a beneficial effect when administered in known and controlled quantities. Such devices and methods are particularly useful in the medical field where treatments for many patients include the administration of a known amount of a substance at predetermined intervals.

Insulin-injecting pumps have been developed for the administration of insulin for those suffering from both type I and II diabetes. Continuous subcutaneous insulin injection and/or infusion therapy with portable infusion device has been adapted for the treatment of diabetes. Such therapy may include the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

There are, however, some drawbacks associated with the use of subcutaneous injection syringes and/or some currently available infusion pumps for the delivery of insulin and other medicaments. Some commercially available pumps may have an interchangeable infusion cartridge containing insulin and/or other medicaments. The correct attachment of this interchangeable infusion cartridge is important for the proper delivery of medicament. For instance, the cartridge may inadvertently become detached or may not be attached to the pump, resulting in possible inaccuracies in treatment and other issues.

Therefore, there is a need for a system and a method for detecting the presence or absence of the infusion cartridge in the infusion pump.

SUMMARY

Disclosed herein are systems and methods for detecting the presence of an interchangeable infusion cartridge in an infusion pump and particularly in a portable or ambulatory infusion pump. In some embodiments, the method may include installing an infusion cartridge in an infusion pump, initiating an infusion cartridge loading sequence, recording loading pulse width modulation (PWM) commands applied to an infusion pump motor, setting a value of threshold PWM commands, comparing values of operational PWM commands applied during pumping operations to the value of the threshold PWM commands, and generating a missing cartridge indication whenever the value of an operational PWM command drops below the value of the threshold PWM commands by a predetermined amount.

In some embodiments an infusion system is provided. The infusion system may be configured for detecting a presence or absence of an infusion cartridge. The infusion system may include an infusion cartridge and an infusion pump. The infusion cartridge may include a delivery mechanism for effectuating delivery of fluid having an axial bore, a spool which may be disposed within the axial bore and axially translatable within the axial bore, and a drug delivery reservoir for storing fluid. The infusion pump may include a drive mechanism and a processor. The processor may be coupled to a memory configured for receiving input data from the memory and using input data for generating operational parameters for the infusion system. Programming may be stored in the memory for execution by a processor to control a closed-loop motor control algorithm. The closed-loop motor control algorithm may be configured for generating PWM commands that operate a motor of the drive mechanism, and to indicate an absence of the infusion cartridge if the value of the operational PWM command falls below the predetermined value the threshold PWM commands.

Certain embodiments are described further in the following description, examples, claims, and drawings. These features of embodiments will become more apparent from the following detailed description when taken in conjunction with the accompanying exemplary drawings.

DETAILED DESCRIPTION

Provided herein are systems, devices and methods for continuous or semi-continuous monitoring of the absence or presence of an interchangeable infusion cartridge in an infusion pump, and particularly in a portable or ambulatory infusion pump utilizing a replaceable cartridge containing insulin and/or other medicaments for the treatment of diabetes. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

It should be noted that labels associated with operations described herein do not necessarily represent an order in a sequence; rather, they are used only to uniquely identify each operation. The words "loaded", "written", and "programmed" are used interchangeably in this document when they refer to a processor or a memory device. The terms "pump" and "infusion pump" may be used interchangeably throughout the document as may be the terms "fluid" and "liquid medicament." In addition, the terms "pulse width modulation (PWM) commands" and "PWM commands" interchangeably represent a series of electrical pulses provided to power an electric motor of the infusion pump. A value of PWM commands generally represents a duty cycle of the series of pulses during a command sequence. For example, if the PWM is 100% with an input voltage of 3.0 volts, the output will be 3.0 volts. If the PWM command is 50%, the output voltage of the same 3.0 volt input would be 1.5 volts.

Figure 2:
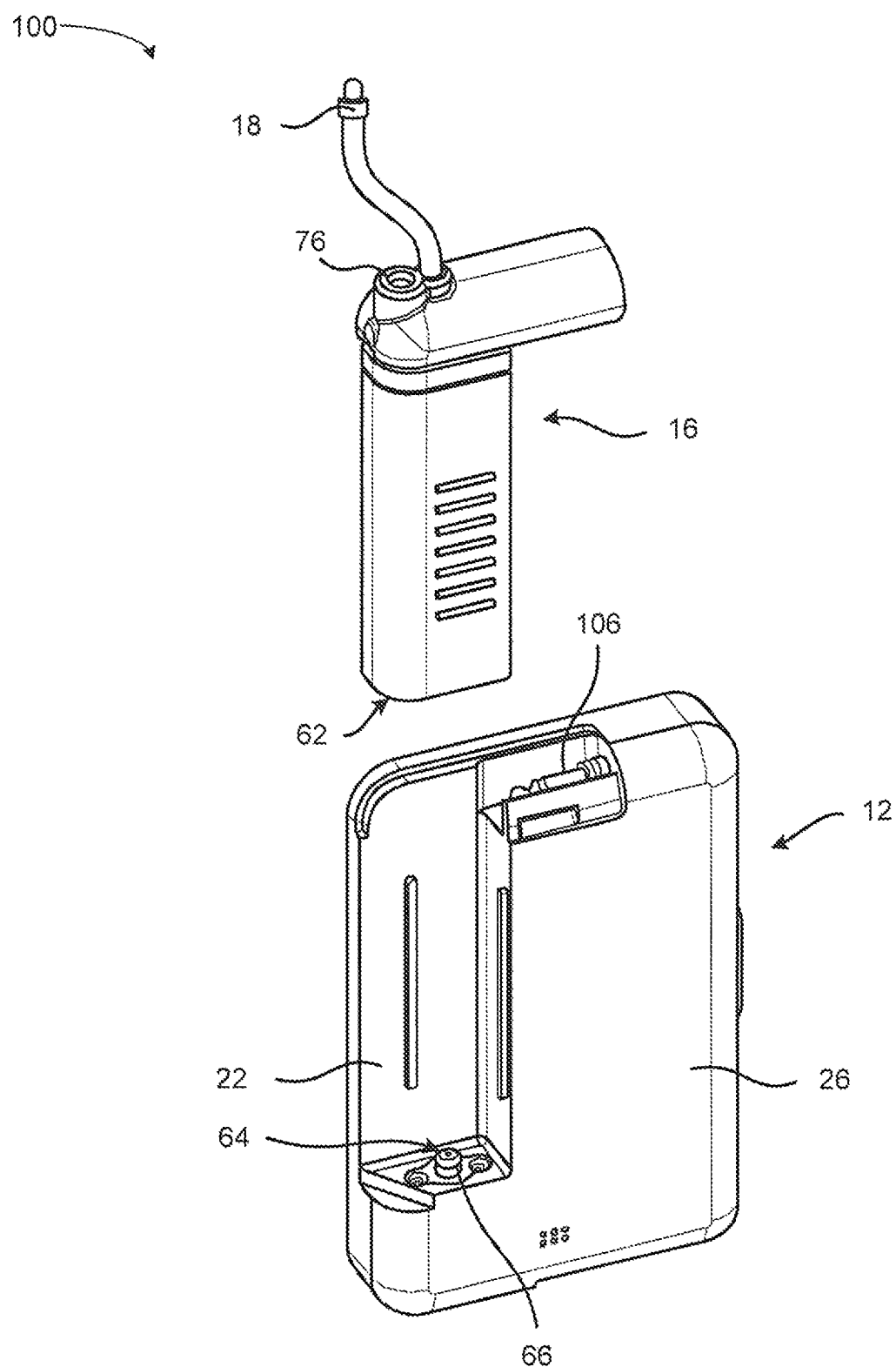
FIG. 2 is an exploded view of an embodiment of an infusion cartridge and an infusion pump with the infusion cartridge removed from the infusion pump.

FIG. 2 depicts an embodiment of an infusion pump system 100 with an infusion cartridge 16 detached from the full-featured infusion pump device 12. The pump 12 can include an attachment mechanism 64, positioned within the first receiving slot 22 that corresponds to a receiving mechanism 62 at an end of the infusion cartridge 16. The attachment and receiving mechanisms can be configured to removably couple to each other to provide for an interchange of cartridges within the slot 22. The coupling keeps an interior of the cartridge and interior of the pump sealed from the surrounding environment such that fluid is retained within the volumes even under significant pressure. This attachment embodiment may be configured to produce a leak free detachable coupling that can withstand significant pressure. The receiving mechanism 62 may be configured to detachably couple with the attachment mechanism 64 such that the infusion cartridge 16 may be removably attached to the housing 26 of the infusion pump 12 for fluid delivery. In this embodiment, the attachment mechanism 64 may include a pneumatic tap 66 having an O-ring or other sealing device. The corresponding receiving mechanism 62 may include a port through which the pneumatic tap 66 may be inserted. A reservoir fill port 76 may be disposed on a top portion of the infusion cartridge 16. In some cases, the desired fluid may be manually dispensed from the interior volume of a syringe or other source, through the reservoir fill port 76 and into the interior volume of the infusion cartridge 16.

Figure 3:
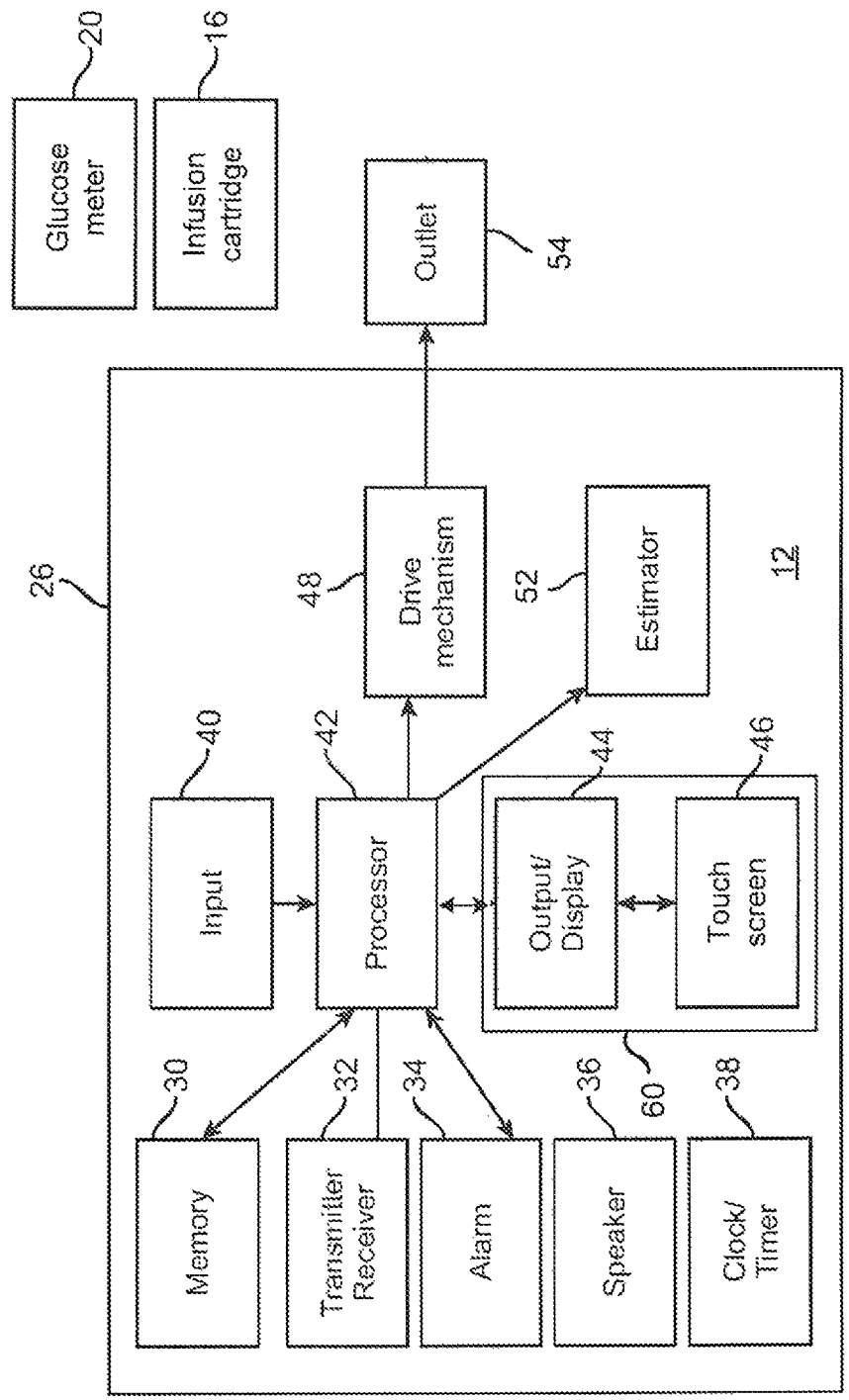
FIG. 3 is a block diagram representing an embodiment of an infusion pump.

FIG. 3 illustrates a block diagram of some features that may be incorporated within the housing 26 of the infusion pump 12. The infusion pump 12 may include a memory device 30, a transmitter/receiver 32, an alarm 34, a speaker 36, a clock/timer 38, an input device 40, a processor 42, an output/ display 44 that can include a user interface such as a graphical user interface (GUI) 60 having a touch sensitive screen 46 with input capability, a drive mechanism 48, and an estimator device 52. The memory device 30 may be coupled to the processor 42 to receive and store input data, and to communicate that data to the processor 42. The input data may include user input data and sensor input data. The input data from the memory device 30 may be used to generate operational parameters for the infusion pump 12. The GUI 60 may be configured for displaying a request for the user to input data, for receiving user input data in response to the request, and communicating that data to the memory. The GUI 60 can also be configured to display a missing infusion cartridge indication/warning as discussed herein.

The processor 42 can function to control the overall operation of the pump. Processor 42 may communicate with and/or otherwise control the drive mechanism, output/display, memory, transmitter/receiver, and the like. Processor 42 of the infusion pump may communicate with a processor of another device, such as a continuous glucose monitor, a remote controller/commander, etc. Processor 42 may include programming that can control the infusion of insulin or other medicament from the cartridge, the data to be displayed by the display, the data to be transmitted via the transmitter, etc. Part of the programming may be configured to control an electric motor 170 depicted in FIG. 4. Processor 42 may also include programming that may allow the processor to receive signals and/or other data from an input device, such as a sensor sensing pressure, temperature, and the like. The processor 42 may be included as a part of infusion pump 12 or may be used in conjunction therewith.

According to an embodiment, a motor control program may be stored in the memory 30 for retrieval by the processor 42 to operate a closed-loop motor control algorithm. The closed-loop motor control algorithm may be configured for generating PWM commands. The PWM commands may be, e.g., a series of uniform amplitude voltage pulses that are used to measure the command input into the motor. The PWM commands may be coupled to the electric motor 170 to power a drive mechanism 48. An embodiment of the motor control algorithm may be a velocity loop algorithm. Such a velocity loop algorithm can be a proportional-integral-derivative (PID) loop in which motor velocity is the controlled output. A value of the PWM commands may be proportional to a load on the electric motor 170. The load may differ greatly, depending on the presence or absence of an infusion cartridge 16. In the case where the infusion cartridge 16 is absent, a smaller load may indicate this absence.

The processor 42 may also include additional programming to allow the processor 42 to learn user preferences and/or user characteristics and/or user history data. For instance, to implement changes in use, suggestions based on detected trends, such as, weight gain or loss, and may include programming allowing the device to generate reports, such as user history, compliance, trending, and/or other such data. Additionally, infusion pump embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pumps, including a high power processor and a low power processor used to maintain programming and pumping functions in low power mode in order to, e.g., save battery life.

Housing 26 of the infusion pump 12 may be functionally associated with an interchangeable and a removable glucose meter 20 and/or infusion cartridge 16. The infusion cartridge 16 may have an outlet port 54 that may be connected to an infusion set (not shown) via an infusion set connector 18 (as shown in FIG. 2).

Figure 1:
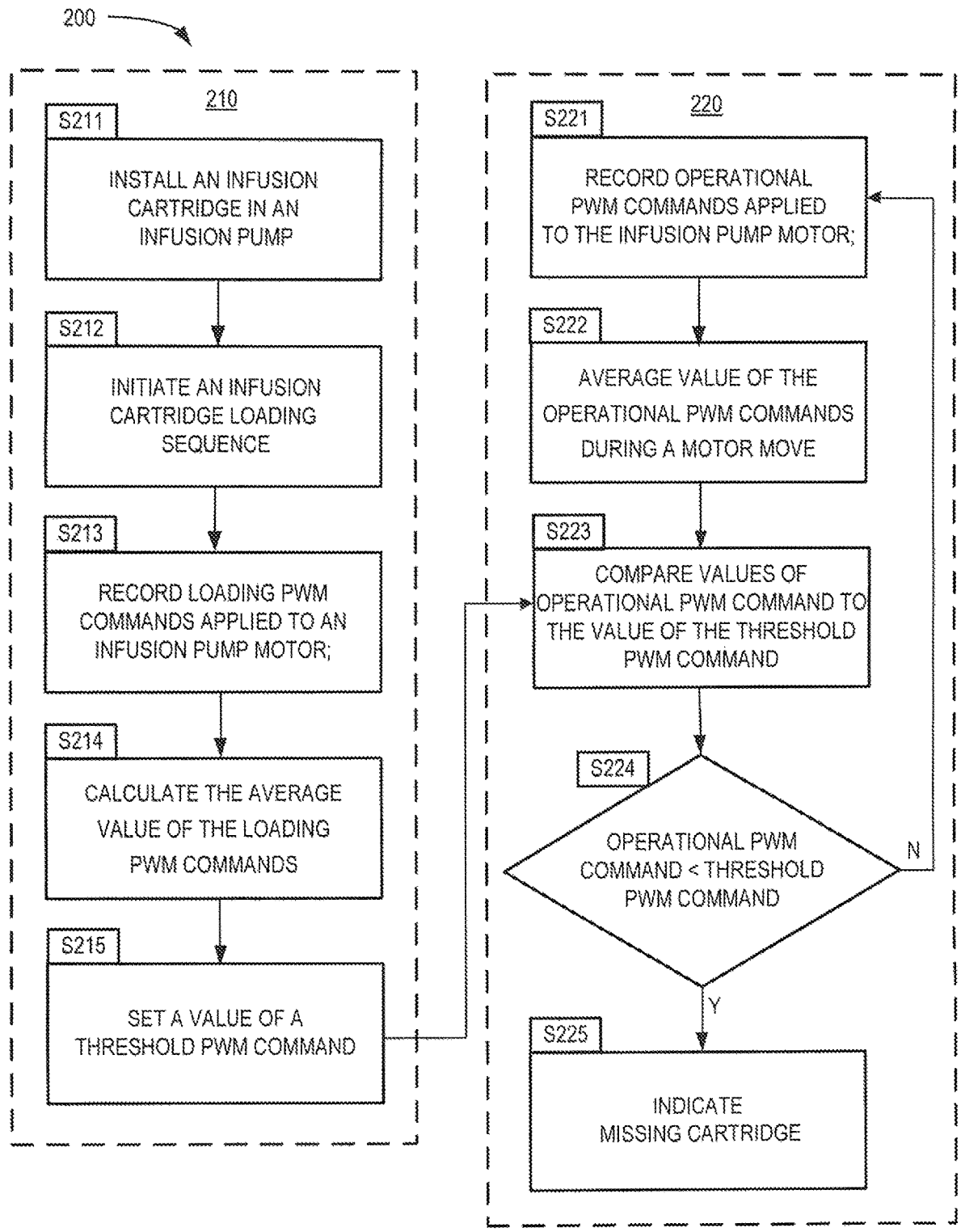
FIG. 1 is a flowchart illustrating a method embodiment for detecting the presence of an interchangeable infusion cartridge in an infusion pump.

Referring now to FIG. 1, a flowchart depicting a top-level view of a method 200 according to embodiments of the present disclosure is illustrated. The method 200 includes detecting the presence or absence of an infusion cartridge in an infusion pump. In some cases method 200 may include two phases, a calibration phase 210 and a pumping phase 220.

Method 200 may start the PWM calibration phase 210 at operation S211. In operation S211, an infusion cartridge may be installed in an infusion pump such as, for example, as described above. In operation S212, an infusion cartridge loading sequence may be initiated. During the loading sequence an electric infusion pump motor, propelling a drive mechanism, may engage a fluid delivery mechanism within the infusion cartridge. The engaged fluid delivery mechanism may represent a specific load on the infusion pump motor. In operation S213, PWM commands applied on the infusion pump motor during the loading sequence may be recorded into memory. For example, the PWM commands may have a percent/value ranging from 20% to 80%. In operation S214, an average value of the recorded PWM commands may be calculated. In operation S215, a value threshold of the PWM commands may be set to be the average value of the recorded PWM commands may be, for example, 52%. Because the PWM configuration procedure 210 can be done each time a cartridge is loaded, the threshold can be set at an appropriate value for each specific cartridge. This is advantageous because the load that each cartridge imparts on the motor can vary greatly.

After a threshold value has been established for a particular cartridge, a pumping phase 220 can be begun. In operations S221 and S222, during the pump phase 220, applied values of the operational PWM commands may be recorded and the average values of those operational PWM commands may be calculated. The PWM commands can be recorded and averaged for the duration of each distinct motor move. In operations S223 and S224, during each subsequent motor move in a pumping cycle, the average value of the operational PWM commands may be compared to the threshold value of the PWM commands. For example, the average value may be somewhere between 40% and 90%.

If an average value of the operational PWM commands is smaller, by a predetermined amount, than the value of the threshold PWM commands, a missing infusion cartridge indication/warning may be generated in operation 225, and the pumping may be halted. In some embodiments, the average value of more than one motor move must deviate from the threshold to generate an alarm. In one embodiment, the alarm is generated if two motor moves in a row generate an average PWM value greater that deviate from the threshold by the predetermined amount. In certain embodiments, the number of motor move values that must cross the threshold to generate an alarm can be adjusted to vary the sensitivity of the alarm. If an average value of the operational PWM commands is larger, by the predetermined value, than the value of threshold PWM commands, the pumping may continue in operation S221. In one example, the predetermined amount may be 10%. Thus, in the example in which the threshold value was 52%, of the average value of the operational commands is below 42%, the alarm is generated.

The predetermined value may be selected and set differently based on a selected pumping speed. For example, for a low pumping speed the predetermined value may be in the range of 20%-40% of the value of the threshold PWM command, for a high pumping speed the predetermined value may be in the range of 40%-60% of the value of the threshold PWM command. In one embodiment, this loop 220 can be conducted continuously in order to indicate that a cartridge is absent as soon as possible when a cartridge is dislodged or removed.

Figure 4:
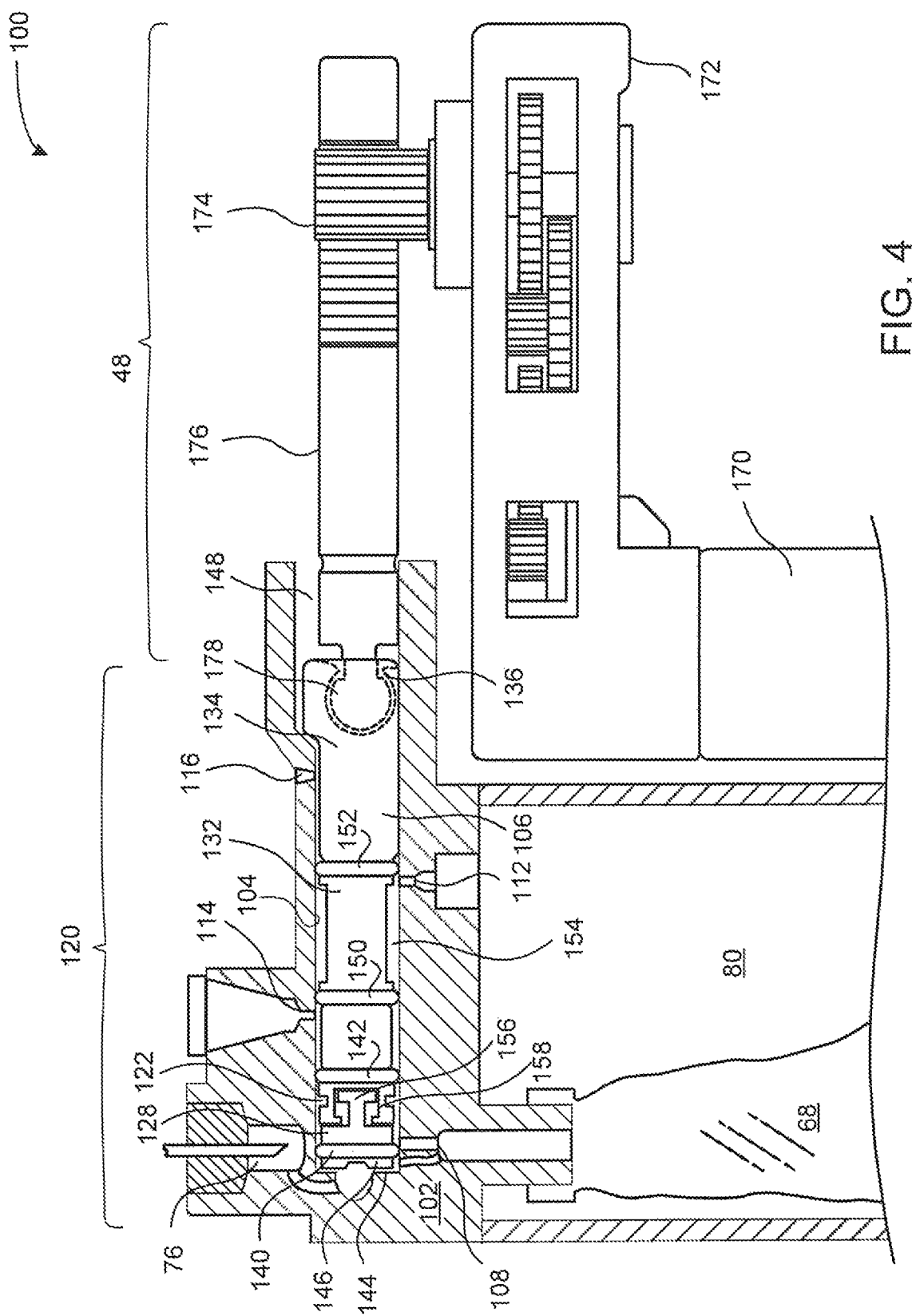
FIG. 4 is an elevation view in partial section of a delivery mechanism embodiment of the infusion cartridge embodiment of FIG. 2 coupled to a drive mechanism embodiment.

FIG. 4 depicts an embodiment of portion of an infusion cartridge such as infusion cartridge 16 including the delivery mechanism 120, as well as a portion of the drive mechanism 48 of an infusion pump such as infusion pump 12 with which the method 200 described above can be employed. The delivery mechanism 120 may be configured to deliver fluid from a collapsible drug delivery reservoir 68 via a collapsible or variable volume element of a spool 106. For the embodiments discussed herein, the variable volume elements may include constrained variable volume elements that are mechanically constrained to vary between a minimum volume and a maximum volume. The delivery mechanism 120 may include a delivery mechanism body 102, or housing, and an axial bore 104 disposed in the delivery mechanism body 102. The axial bore 104, may have a substantially round transverse cross section that may include a distal end 144, a proximal end 148 disposed towards the drive mechanism 48 of the infusion pump system 100, a reservoir inlet port 108, a fluid outlet port 114, a vent inlet port 112, and a vent outlet port 116. The spool 106 has a distal end 146 and may also have a substantially round transverse cross section, which may be slidingly disposed within the axial bore 104 and may form a constrained variable volume 122 and a second vented volume 154 with the axial bore 104. The drive mechanism 48 may include a rack and pinion mechanism 174 actuated by an electric motor 170 through a gear box 172.

The constrained variable volume 122 of the delivery mechanism 120 may be positionable to overlap the reservoir inlet port 108 independent of an overlap of the fluid outlet port 114. The constrained variable volume 122 may be formed between a first seal 140 around the spool 106, a second seal 142 around the spool 106, an outer surface of the spool body between the first and second seal 140 and 142 and an interior surface of the axial bore 104 between the first and second seal 140 and 142. The first and second seals 140 and 142 are axially moveable relative to each other so as to increase a volume of the constrained variable volume 122 when the first and second seals 140 and 142 are moved away from each other, and decrease the constrained variable volume 122 when the first and second seals 140 and 142 are moved closer together.

The second seal 142 may be disposed on a proximal section 134 of the spool 106 and may move in conjunction with movement of the proximal section 134 of the spool 106. A proximal end of the spool 136 may be coupled to a ball portion 178 of a drive shaft 176 of the drive mechanism 48 of the infusion pump 12. The drive mechanism 48 may include a rack and pinion mechanism 174 actuated by an electric motor 170 through a gear box 172. As such, the second seal 142 may move or translate axially in step with axial translation of the spool 106 and drive shaft 176. The first seal 140, however, may be disposed on a distal section 128 of the spool 106 which may be axially displaceable with respect to the main section 190 of the spool 106. The distal section 128 of the spool 106 may be coupled to the main section of the spool by an axial extension 156 that may be mechanically captured by a cavity 158 in the main section 132 of the spool 106. This configuration may impart a predetermined amount of controlled axial movement between the distal section 128 of the spool and the main section 132 of the spool 106 and may translate the constrained variable volume 122 from the reservoir inlet port 108 to the fluid outlet port 114. This configuration may expand or contract the constrained variable volume 112 of the spool 106 by exerting translational axial force through a boundary section of the constrained variable volume 122.

For some embodiments, a volume of a "bucket" of fluid dispensed by a complete and full dispense cycle of the spool 106 may be approximately equal to the cross-sectional area of the axial bore 104 multiplied by the length of displacement of the captured axial extension of the spool for the distal section 128. The complete bucket of fluid may also be dispensed in smaller sub-volumes in increments as small as a resolution of the drive mechanism 48 allows. For some embodiments, a dispense volume or bucket defined by the constrained variable volume 122 of the delivery mechanism 120 may be divided into about 10 to about 100 sub-volumes to be delivered or dispensed. In some cases, the maximum axial displacement between the distal section 128 and main section of the spool 132 may range from about 0.01 inch to about 0.04 inch; more specifically, from about 0.018 inch to about 0.022 inch.

For some embodiments, the axial bore 104 of the delivery mechanism may have a transverse dimension or diameter ranging from about 0.04 inches to about 0.5 inches; more specifically, from about 0.08 inches to about 0.15 inches. For some embodiments, the spool 106 may have a length ranging from about 10 mm to about 40 mm; more specifically, from about 15 mm to about 20 mm. The spool 106 and housing of the delivery mechanism 48 may be made from any suitable material or materials, including polymers or plastics such as polycarbonate, PEEK, thermoplastics, cyclic olefin copolymer, and the like. In some cases, the seals disposed on the spool may have an outer transverse dimension or diameter that may be slightly larger than that of the spool 106. In some instances, the seals on the spool may have an axial thickness ranging from about 0.01 inches to about 0.03 inches and may be made from materials such as butyl, silicone, polyurethanes or the like having a shore hardness ranging from about 65A to about 75A and, more specifically, about 70A.

In some instances, a second vented volume 154 of the delivery mechanism 120 may be formed by the spool 106 and axial bore 104 of the delivery mechanism 48. The second vented volume 154 may be formed by a third seal 150 disposed around the spool 106 and a fourth seal 152 also disposed around the spool and axially separated from the third seal 150. The axial separation between the third and fourth seals 150 and 152 forming the second vented volume 154 may be greater than the axial separation between the vent inlet port 112 and vent outlet port 116 of the axial bore 104 in some instances. The second vented volume 154 may be formed by an outside surface of the spool 106 between the third and fourth seals 150 and 152 and an inside surface of the axial bore 104 between the third and fourth seals 150 and 152.

The second vented volume 154 may be axially displaceable with the movement of the spool 106 and may also be positionable by such axial displacement in order to simultaneously overlap the second vented volume 154 with the vent inlet port 112 and the vent outlet port 116 of the axial bore 104. Such an overlap of both the vent inlet port 112 and the vent outlet port 116 may put these ports in fluid communication with each other, and may allow an equilibration of pressure between the first vented volume 80 of the infusion cartridge 16 and the environment surrounding the vent outlet port 116. In most cases, the vent outlet port 116 may be in communication with the atmosphere and air may pass from the environment surrounding the vent outlet port 116, through the second vented volume 154 of the axial bore 104, and into the first vented volume 80 to replace the fluid dispensed subsequent to the last vent cycle. When the vent inlet port 112 and vent outlet port 116 do not share a common volume formed by the spool 106 and axial bore 104 of the delivery mechanism 120, they are typically isolated and no venting of the first vented volume 80 may take place.

In operation, the spool 106 defines one or more volumes between the spool 106, the axial bore 104 and the circumferential seals 140, 142, 150 and 152 disposed on the spool of the delivery mechanism 120. The spool 106 is typically translated in a proximal and distal direction in order to move the volumes into and out of communication with the various ports of the axial bore 104. This axial movement in alternating proximal and distal directions of the spool 106 within the axial bore 104 may be used to put the various ports in fluid communication with translatable volumes of the delivery mechanism 120. For reliable operation, it may be desirable in some circumstances for the spool 106 and the circumferential seals 140, 142, 150 and 152 disposed about the spool 106 to move smoothly within the axial bore 104 of the delivery mechanism 120 while maintaining a seal between an outside surface of the spool 106 and an inside surface of the axial bore 104. It may also be desirable for the circumferential seals 140, 142, 150 and 152 disposed on the spool 106 to move axially back and forth within the axial bore 104 while maintaining a seal and with a minimum of friction. Achieving these features of the spool 106 may be facilitated with the use of particular seal configurations or gland configurations used to house the seals of the spool embodiments.

The delivery mechanism 120 may be configured to deliver fluid from the reservoir 68. The delivery mechanism 120 may include a delivery mechanism body 102, or housing, and the axial bore 104 disposed in the delivery mechanism body 102. The axial bore 104 may have a substantially round transverse cross section. The spool 106 may also have a substantially round transverse cross section, and may be slidingly disposed within the axial bore 104. The drive mechanism 48 may include a rack and pinion mechanism 174 actuated by an electric motor 170 through a gear box 172.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

What is claimed is:

1. A method for detecting a presence of an infusion cartridge in an infusion pump, comprising:
    installing the infusion cartridge in the infusion pump;
    initiating an infusion cartridge loading sequence;
    recording loading pulse width modulation (PWM) commands applied to an infusion pump motor during the infusion cartridge loading sequence;
    setting a value of threshold PWM commands based on the loading PWM commands applied to the infusion pump motor during the infusion cartridge loading sequence;
    generating operational PWM commands as electrical command input into the infusion pump motor causing the infusion pump motor to operate a drive mechanism of the infusion pump;
    controlling a velocity output of the infusion pump motor with a velocity loop algorithm by the generating the operational PWM commands as the electrical command input into the infusion pump motor;
    comparing values of the operational PWM commands that are generated as the electrical command input into the infusion pump motor during pumping operations to the value of the threshold PWM commands; and
    generating a missing cartridge indication if the values of the operational PWM commands drop below the value of the threshold PWM commands by a predetermined amount.

2. The method of claim 1, wherein the value of the threshold PWM commands is an average value of the loading PWM commands.

3. The method of claim 1, wherein the values of the operational PWM commands are average values of the loading PWM commands of each subsequent motor move during a pumping cycle.

4. The method of claim 1, wherein the operational PWM commands are uniform amplitude voltage pulses.

5. The method of claim 1, where the predetermined amount is based on a pumping speed of the pumping operations.

6. The method of claim 1, wherein the predetermined amount is between 20% and 40% of the value of the threshold PWM commands.

7. The method of claim 1, wherein the predetermined amount is between 40% and 60% of the value of the threshold PWM commands.

8. The method of claim 1, wherein the generating the missing cartridge indication generates the missing cartridge indication on a user interface of the infusion pump.

9. The method of 1, wherein the values of the operational PWM commands as the electrical command input are proportional to an output load on the motor.

10. The method of claim 1, wherein a value of each of the operational PWM commands compared to the value of the threshold PWM commands is a duty cycle of a series of electrical pulses provided as the electrical command input to power the infusion pump motor for each motor move of a pumping cycle.

11. The method of claim 1, wherein the value of each of the operational PWM commands compared to the value of the threshold PWM commands is a unitless number.

12. A method for detecting a presence of an infusion cartridge in an infusion pump, comprising:
    storing a threshold value of PWM commands;
    executing a closed loop motor control algorithm to generate operational PWM commands, the operational PWM commands representing a measure of electrical command input into an electric motor of the infusion pump that cause the electric motor to power a drive mechanism of the infusion pump;
    controlling a velocity output of the electric motor with the operational PWM commands that are generated as the electrical command input into the electric motor;
    operating the drive mechanism of the infusion pump in response to the operational PWM commands;
    comparing values of the operational PWM commands that are generated as the electrical command input into the electric motor while operating the drive mechanism to the threshold value of PWM commands; and
    generating a missing cartridge indication if the values of the operational PWM commands drop below the threshold value by a predetermined amount.

13. The method of claim 12, wherein the values of the operational PWM commands are proportional to a load on the electric motor.

14. The method of claim 12, further comprising:
    initiating an infusion cartridge loading sequence; and
    recording loading PWM commands applied to the electric motor during the infusion cartridge loading sequence.

15. The method of claim 14, wherein the threshold value is an average value of the loading PWM commands.

16. The method of claim 12, wherein the values of the operational PWM commands are average values of PWM commands of each subsequent motor move during a pumping cycle.

17. The method of claim 12, wherein the operational PWM commands are uniform amplitude voltage pulses.

18. The method of claim 12, where the predetermined amount is based on a pumping speed of pumping operations.

19. The method of claim 12, wherein the predetermined amount is between 20% and 40% of the threshold value of PWM commands.

20. The method of claim 12, wherein the predetermined amount is between 40% and 60% of the threshold value of PWM commands.

21. The method of claim 12, wherein the generating the missing cartridge indication generates the missing cartridge indication on a user interface of the infusion pump.

22. The method of claim 11, wherein the unitless number is a percentage.

23. The method of claim 12, wherein a value of each of the operational PWM commands compared to the threshold value of PWM commands is a duty cycle of a series of electrical pulses provided as input to power the electric motor for each motor move of a pumping cycle.

24. The method of claim 12, wherein a value of each of the operational PWM commands compared to the threshold value of PWM commands is a unitless number.

25. The method of claim 24, wherein the unitless number is a percentage.

* * * * *